US009468407B2

(12) United States Patent
Hoitink et al.

(10) Patent No.: US 9,468,407 B2
(45) Date of Patent: Oct. 18, 2016

(54) CATHETER WITH DISTAL SECTION HAVING SIDE-BY-SIDE LOOPS

(71) Applicant: Biosense Webster (Israel) Ltd., Yokneam (IL)

(72) Inventors: Ryan Hoitink, Pasadena, CA (US); Shubhayu Basu, Anaheim, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 214 days.

(21) Appl. No.: 14/292,635

(22) Filed: May 30, 2014

(65) Prior Publication Data

US 2015/0342531 A1 Dec. 3, 2015

(51) Int. Cl.
*A61B 5/042* (2006.01)
*A61B 18/14* (2006.01)
*A61B 5/00* (2006.01)
*A61B 18/00* (2006.01)

(52) U.S. Cl.
CPC ........... *A61B 5/6856* (2013.01); *A61B 5/0422* (2013.01); *A61B 18/1492* (2013.01); *A61B 2018/0016* (2013.01); *A61B 2018/00351* (2013.01); *A61B 2018/00375* (2013.01); *A61B 2018/00577* (2013.01); *A61B 2018/00642* (2013.01); *A61B 2018/00839* (2013.01); *A61B 2018/1467* (2013.01); *A61B 2018/1475* (2013.01)

(58) Field of Classification Search
CPC .................... A61B 5/0422; A61B 2018/1407; A61B 5/6856
See application file for complete search history.

(56) References Cited

U.S. PATENT DOCUMENTS

| 3,866,615 | A | * | 2/1975 | Hewson | A61N 1/0587 607/10 |
|---|---|---|---|---|---|
| RE34,502 | E | | 1/1994 | Webster, Jr. | |
| 5,282,845 | A | * | 2/1994 | Bush | A61N 1/0587 607/127 |
| 5,454,370 | A | * | 10/1995 | Avitall | A61B 5/0422 600/374 |
| 5,897,529 | A | | 4/1999 | Ponzi | |
| 5,938,694 | A | * | 8/1999 | Jaraczewski | A61B 5/0422 600/373 |

(Continued)

FOREIGN PATENT DOCUMENTS

| CN | 103142305 A | 6/2013 |
|---|---|---|
| WO | WO 01/19270 A1 | 3/2001 |

OTHER PUBLICATIONS

EPO Search Report for EP 15169910.5 dated Oct. 14, 2015, 6 pgs.

*Primary Examiner* — Lee S Cohen
(74) *Attorney, Agent, or Firm* — Lewis Roca Rothgerber Christie LLP

(57) ABSTRACT

The catheter allows mapping and/or ablation of the area around two or more PV ostia at the same time, with a single placement of a distal section of the catheter having a 2D configuration resembling an infinity or lazy 8 symbol. The catheter has an elongated catheter body, a distal section having at least a flexible elongated member with shape memory, the member being configured to assume a 2D configuration resembling an infinity symbol, and at least one electrode mounted on the member. The 2D configuration resembles a first loop and a second loop, wherein the first and second loops are side-by-side, generally extending in a common plane.

16 Claims, 15 Drawing Sheets

(56) References Cited

U.S. PATENT DOCUMENTS

| | | |
|---|---|---|
| 5,964,757 A | 10/1999 | Ponzi |
| 6,106,522 A * | 8/2000 | Fleischman .......... A61B 5/0422 374/E1.005 |
| 6,123,699 A | 9/2000 | Webster, Jr. |
| 6,171,277 B1 | 1/2001 | Ponzi |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,210,407 B1 | 4/2001 | Webster |
| 6,267,746 B1 | 7/2001 | Bumbalough |
| 6,771,996 B2 | 8/2004 | Bowe et al. |
| 6,972,016 B2 | 12/2005 | Hill, III et al. |
| 6,973,339 B2 | 12/2005 | Govari |
| 7,366,557 B2 * | 4/2008 | Bautista ............... A61B 5/0422 600/372 |
| 7,740,629 B2 | 6/2010 | Anderson et al. |
| 8,002,771 B2 | 8/2011 | Cox et al. |
| 8,545,495 B2 | 10/2013 | Scheib |
| 2005/0228468 A1 | 10/2005 | Macoviak et al. |
| 2007/0219546 A1 | 9/2007 | Mody et al. |
| 2014/0187894 A1 * | 7/2014 | Bui ........................ A61B 5/042 600/373 |
| 2014/0276755 A1 * | 9/2014 | Cao ......................... A61N 5/00 606/33 |
| 2015/0141785 A1 * | 5/2015 | Hayam ................ A61B 5/4836 600/374 |

\* cited by examiner

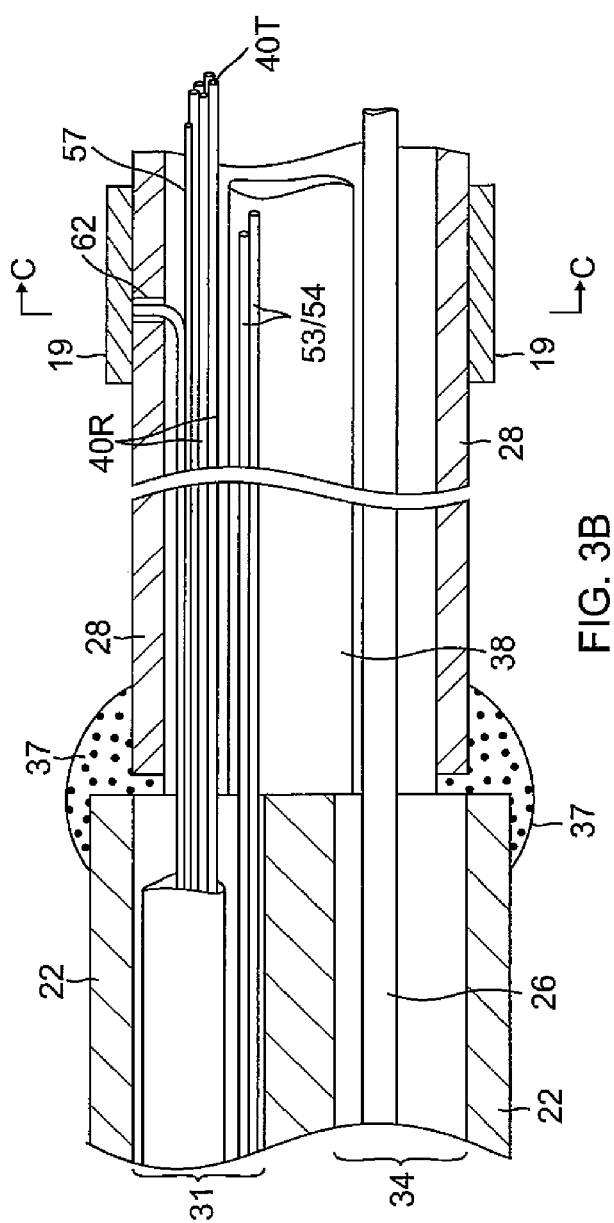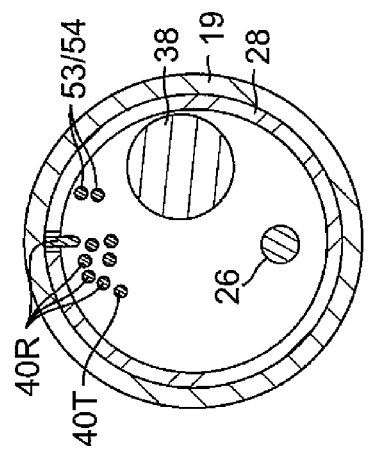

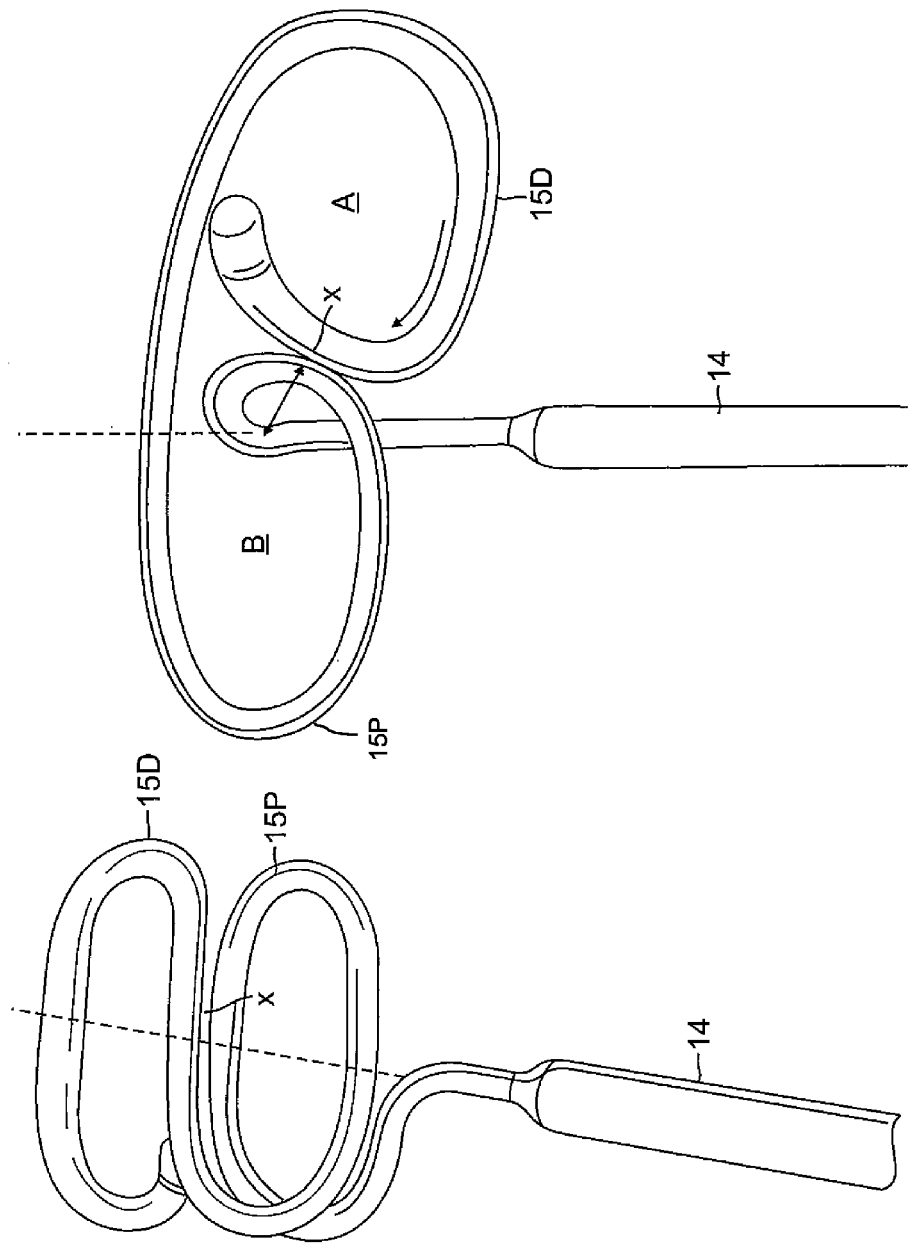

CATHETER WITH DISTAL SECTION HAVING SIDE-BY-SIDE LOOPS

FIELD OF INVENTION

This invention relates to catheters, in particular, pulmonary catheters for ablation and tissue diagnostics.

BACKGROUND

Cardiac arrhythmia, such as atrial fibrillation, occurs when regions of cardiac tissue abnormally conduct electric signals to adjacent tissue, thereby disrupting the normal cardiac cycle and causing asynchronous rhythm. Important sources of undesired signals are located in the tissue region along the pulmonary veins of the left atrium and in the superior pulmonary veins. In this condition, after unwanted signals are generated in the pulmonary veins or conducted through the pulmonary veins from other sources, they are conducted into the left atrium where they can initiate or continue arrhythmia.

Procedures for treating arrhythmia include surgically disrupting the origin of the signals causing the arrhythmia, as well as disrupting the conducting pathway for such signals. More recently, it has been found that by mapping the electrical properties of the endocardium and the heart volume, and selectively ablating cardiac tissue by application of energy, it is possible to cease or modify the propagation of unwanted electrical signals from one portion of the heart to another. The ablation process destroys the unwanted electrical pathways by formation of non-conducting lesions.

In this two-step procedure—mapping followed by ablation—electrical activity at points in the heart is typically sensed and measured by advancing a catheter containing one or more electrical sensors into the heart, and acquiring data at a multiplicity of points. These data are then utilized to select the target areas at which ablation is to be performed.

A lasso catheter is disclosed in commonly assigned U.S. Pat. No. 6,973,339, which is herein incorporated by reference. Particularly adapted for mapping and ablation a pulmonary vein or its ostium, the lasso catheter can decrease diagnostic time, but its use is limited to mapping one vein or ostium at a time. There being four pulmonary veins in the left atrium, there is a desire for a catheter to be able to simultaneously map and/or ablate more than a single PV ostium.

SUMMARY OF THE INVENTION

The catheter of the present invention is intended to allow mapping and/or ablation of the area around two or more PV ostia at the same time, with a single placement of a distal section of the catheter having a 2D configuration resembling an infinity or and upright or lazy "8" symbol.

In one embodiment, the catheter has an elongated catheter body, a distal section having at least a flexible elongated member with shape memory, the member being configured to assume a 2D configuration resembling an infinity symbol, and at least one electrode mounted on the member. The 2D configuration resembles a first loop and a second loop, wherein the first and second loops are side-by-side, generally extending in a common plane.

In a detailed embodiment, flexible elongated member has a distal S configuration and a proximal S configuration, wherein the S configurations are stacked on each other, and one of the S configurations is reversed. In another detailed embodiment, the flexible elongated member has a distal O configuration, a first proximal C configuration and a second proximal C configuration, wherein the first and second C configurations face each other. Alternatively, the flexible elongated member has a distal C configuration, a less proximal O configuration and a more proximal C configuration, wherein the distal and proximal C configurations form a first loop and the proximal O configuration forms the second loop. In yet another detailed embodiment, the member has a distal O configuration that forms the first loop and a proximal O configuration forms the second loop.

The distal section may also have two flexible elongated members, each extending from the deflection section and defining an angle of about 180 degrees from each other to form the 2D configuration of a first loop and a second loop extending generally in a common plane.

BRIEF DESCRIPTION OF THE DRAWINGS

These and other features and advantages of the present invention will be better understood by reference to the following detailed description when considered in conjunction with the accompanying drawings wherein:

FIG. 3B is a side cross-sectional view of the junction of FIG. 3A, taken along a second diameter generally perpendicular to the first diameter.

FIG. 3C is an end cross-sectional view of the distal section of FIGS. 3A and 3B, taken along line C-C.

FIG. 7A is a perspective view of a distal section, in accordance with another embodiment of the present invention.

FIG. 7B is a perspective view of a distal section, in accordance with yet another embodiment of the present invention.

DETAILED DESCRIPTION OF THE INVENTION

Figure 1:
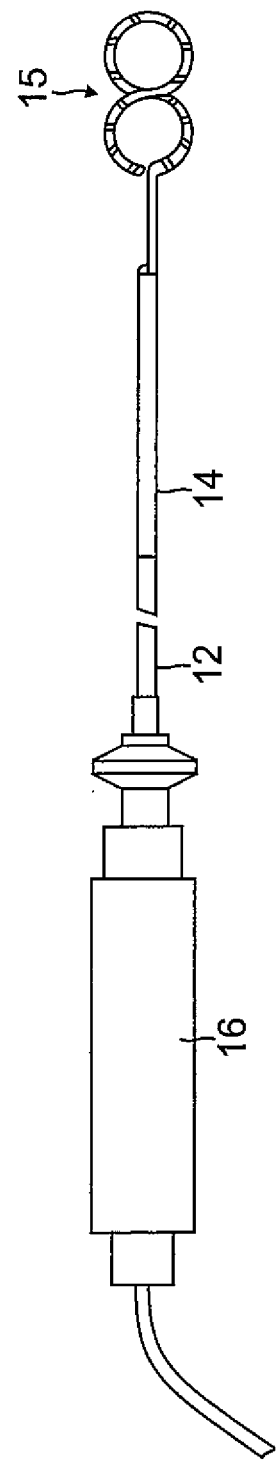
FIG. 1 is a perspective view of a catheter of the present invention, in accordance with one embodiment.

As shown in FIG. 1, the catheter 10 comprises an elongated catheter body 12, an intermediate deflection section 14, a distal section 15, and a deflection control handle 16 attached to the proximal end of the catheter body 12. In accordance with a feature of the present invention, the distal section 15 has at least one flexible tubular member, with shape memory of a predetermined two-dimensional (2D) configuration, which when deployed, or otherwise released from external force(s) that can generally straighten the flexible tubular distal section, assumes the 2D configuration comprising at least two, side-by-side loops resembling an "infinity" symbol or a "lazy 8." The deployed 2D configuration of two or more, side-by-side loops enables the distal section 15 to contact two or more pulmonary vein (PV) regions, including the ostia, in a generally simultaneous manner. Each loop carries one or more electrodes, for example, a tip electrode 17 and at least one ring electrode 19 for obtaining electrical data from the PV regions and/or ablating the same.

Figure 2A:
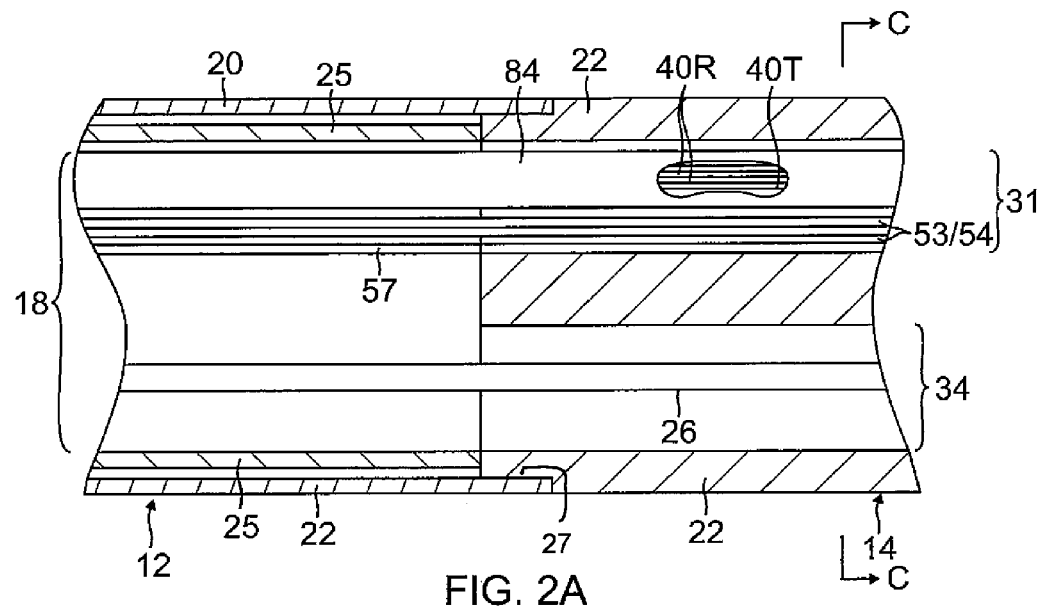
FIG. 2A is a side cross-sectional view of the catheter of FIG. 1, including a junction between a catheter body and a deflection section, taken along a first diameter.
Figure 2B:
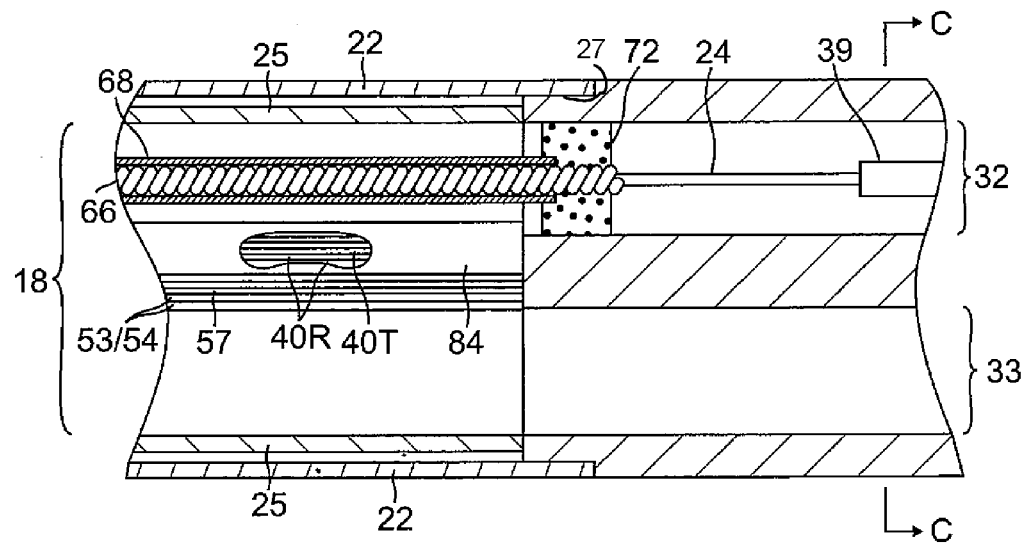
FIG. 2B is a side cross-sectional view of the catheter of FIG. 1, including the junction of FIG. 2A, taken along a second diameter generally perpendicular to the first diameter.

With reference to FIGS. 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably about 7 french. Likewise, the thickness of the outer wall 20 is not critical, but is thin enough so that the central lumen 18 can accommodate a puller wire, one or more lead wires, and any other desired wires, cables or tubes. If desired, the inner surface of the outer wall 20 is lined with a stiffening tube 25 to provide improved torsional stability. A particularly preferred catheter has an outer wall 20 with an outer diameter of from about 0.090 inch to about 0.94 inch and an inner diameter of from about 0.061 inch to about 0.065 inch.

Figure 2C:
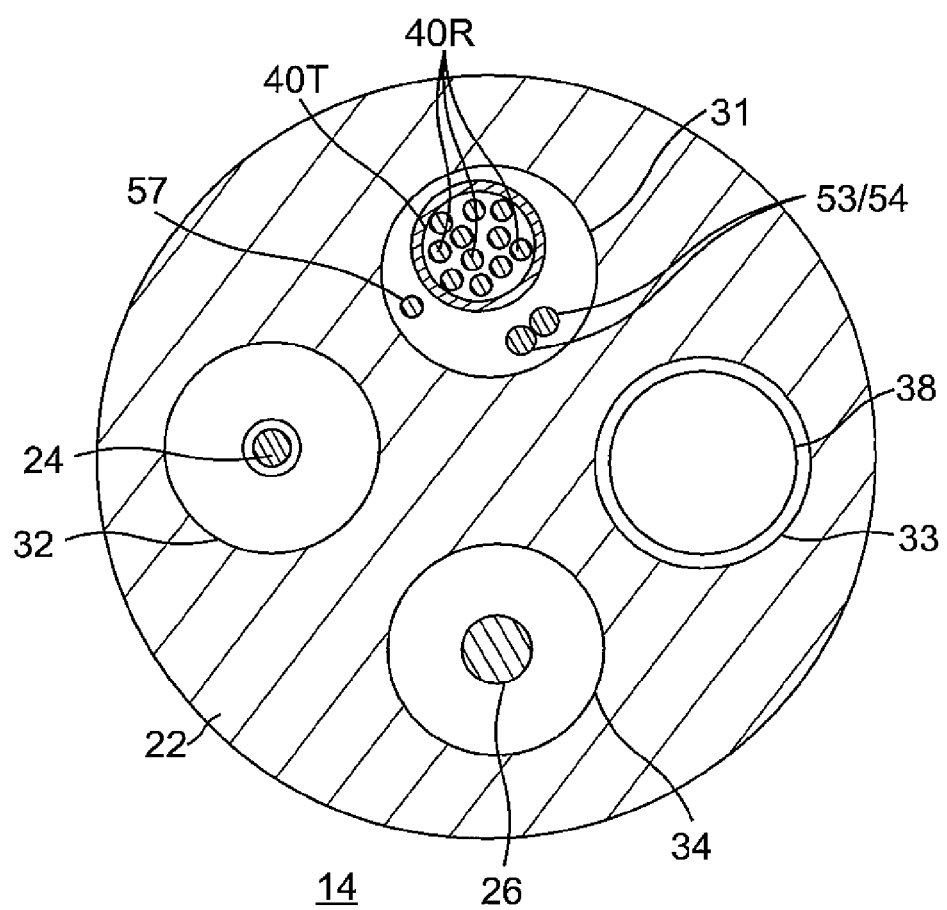
FIG. 2C is an end cross-sectional view of the deflection section of FIGS. 2A and 2B, taken along line C-C.

As shown in FIGS. 2A, 2B and 2C, the intermediate section 14 comprises a short section of tubing 22 having multiple lumens, for example, four lumens 31, 32, 33 and 34. The first lumen 31 carries one or more lead wires 40 or other wires discussed further below, the second lumen 32 carries a puller wire 24, and the third lumen 33 near its distal end carries a proximal end of a shape-memory support member 38. The fourth lumen 34 carries a cable 26 for an electromagnetic position sensor 30. The tubing 22 is made of a suitable non-toxic material that is preferably more flexible than the catheter body 12. One suitable material for the tubing 22 is braided polyurethane, i.e., polyurethane with an embedded mesh of braided stainless steel or the like. The size of each lumen is not critical, but is sufficient to house the lead wires, puller wire or support member.

The useful length of the catheter, i.e., that portion that can be inserted into the body excluding the distal section 15, can vary as desired. Preferably the useful length ranges from about 110 cm to about 120 cm. The length of the intermediate section 14 is a relatively smaller portion of the useful length, and preferably ranges from about 3.5 cm to about 10 cm, more preferably from about 5 cm to about 6.5 cm.

A preferred means for attaching the catheter body 12 to the intermediate section 14 is illustrated in FIGS. 2A and 2B. The proximal end of the intermediate section 14 comprises an outer circumferential notch 27 that receives the inner surface of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

Figure 3A:
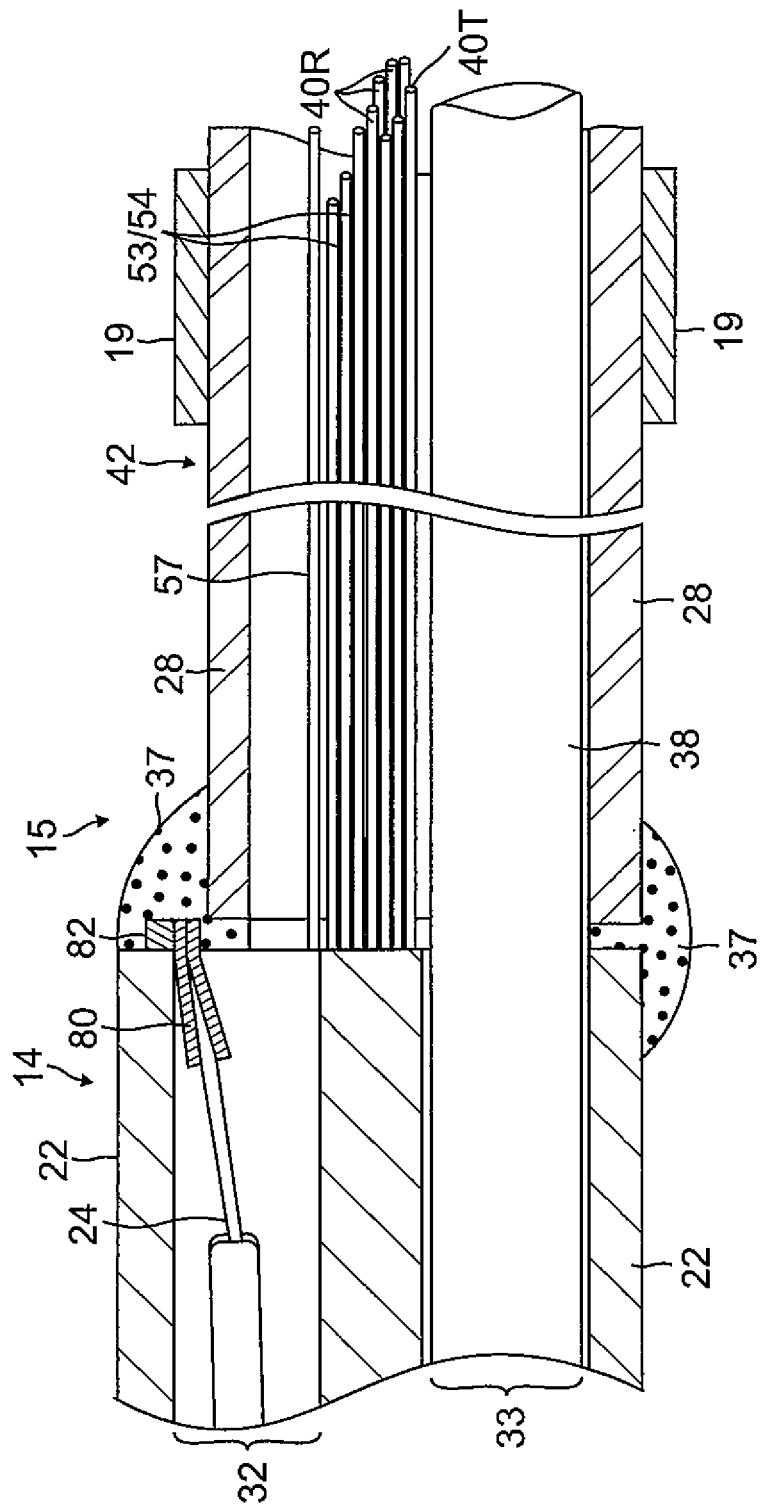
FIG. 3A is a side cross-sectional view of the catheter of FIG. 1, including a junction between the deflection section and a distal section, taken along a first diameter.

Extending from the distal end of the intermediate section 14 is the distal section 15, as shown in FIGS. 3A, 3B and 3C. Each flexible elongated member 42 of the distal section 15 comprises an elongated support member 38 with shape memory, and a non-conductive covering or tubing 28 covering the support member 38. The member 42 has a length ranging from about 20 mm to about 300 mm, more preferably about 100 mm to about 200 mm, still more preferably about 120 mm, but can vary as desired. Each loop formed by a respective member 42 has a diameter or width ranging from about 4 mm to about 40 mm, more preferably about 10 mm to about 25 mm, still more preferably about 17 mm, but can vary as desired. The support member 38 is made of a material having shape-memory, i.e., that can be temporarily straightened or bent out of its original shape upon exertion of a force and is capable of substantially returning to its original shape upon removal of the force. One suitable material for the support member 38 is a nickel/titanium alloy. Such alloys typically comprise about 55% nickel and 45% titanium, but may comprise from about 54% to about 57% nickel with the balance being titanium. A nickel/titanium alloy is nitinol, which has excellent shape memory, together with ductility, strength, corrosion resistance, electrical resistivity and temperature stability. The non-conductive covering 28 can be made of any suitable material, and is preferably made of a biocompatible plastic such as polyurethane or PEBAX. If desired, the support member 38 can be eliminated and the distal end of the non-conductive covering 28 can be pre-formed to have the desired curvature or configuration.

At a junction of the intermediate section 14 and the distal section 15, the non-conductive covering 28 is attached to the tubing 22 of the intermediate section by glue 37 or the like. The support member 38 extends from the third lumen 33 into the non-conductive covering 28. The proximal end of the support member 38 terminates within the third lumen 34, approximately about 5 mm from the distal end of the tubing 22, so as not to adversely affect the ability of the intermediate section 14 to deflect. However, if desired, the proximal end of the support member 38 can extend into the catheter body 12.

With reference to FIGS. 4A-4E, the distal section 15 (illustrated without any tip or ring electrodes for clarity) comprises a generally linear (one dimensional) but flexible tubular member 42 with shape memory, as provided by the support member 38, of a predetermined 2D configuration (FIG. 4E) comprising at least two side-by-side loops A and B that are generally coplanar with each other and are generally joined or intersecting (or having an appearance of being joined or intersecting) with each other at their closest location X to resemble an "infinity" symbol or a lazy 8 (used interchangeably herein). It is understood that the term "loop" as used herein does not necessarily mean a closed configuration accomplished with a single continuous flexible tubular member, but rather that one or more flexible tubular members may be configured to resemble or have the appearance of a loop for purposes of enabling contact with tissue surface in a pattern of a generally closed configuration so as to surround or encircle a respective region, for example, a respective PV ostium. In other words, it is understood that the term "loop" is used with respect to the resulting "stamp" or "imprint" pattern of one or more flexible tubular members on tissue surface of purposes of mapping and/or ablation a region, for example, a PV ostium.

Figure 4A:
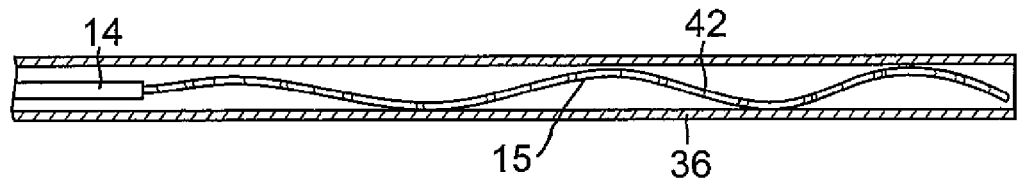
FIG. 4A is a side cross-sectional view of a distal section, in accordance with an embodiment of the present invention, extending through a guiding sheath.
Figure 4B:
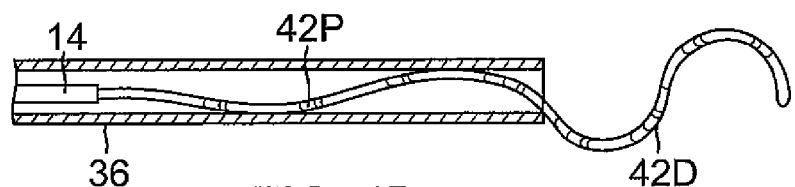
FIG. 4B is a side cross-sectional view of the distal section of FIG. 4A partially deployed from the guiding sheath.
Figure 4C:
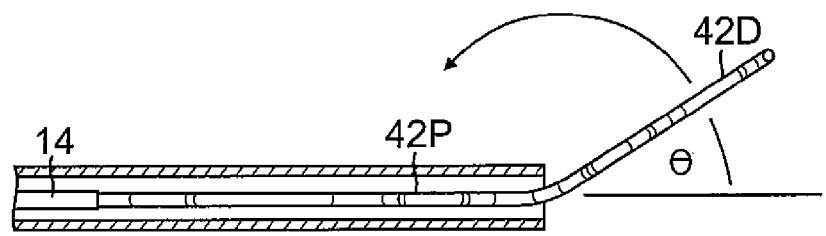
FIG. 4C is a top side cross-sectional view of the distal section of FIG. 4B.
Figure 4D:
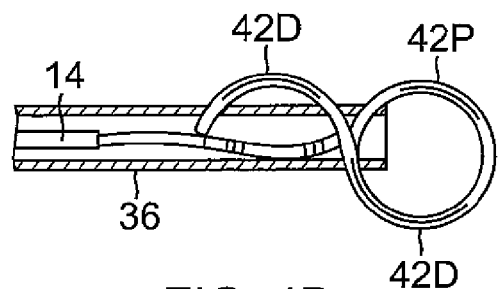
FIG. 4D is a side cross-sectional view of the distal section further deployed from the guiding sheath.
Figure 4E:
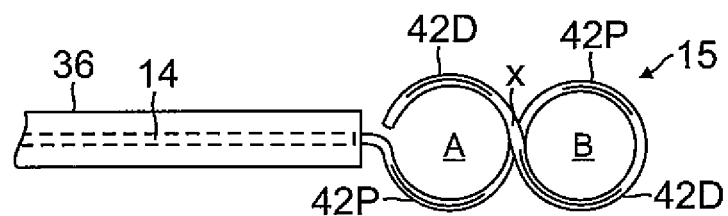
FIG. 4E is a side view of the distal section fully deployed from the guiding sheath.
Figure 4F:
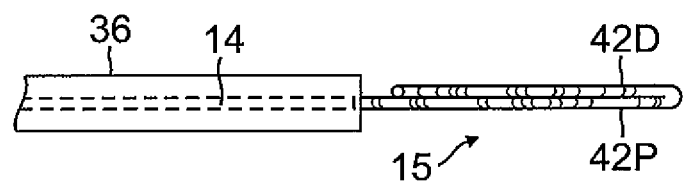
FIG. 4F is a top view of the distal section of FIG. 4E
Figure 4G:
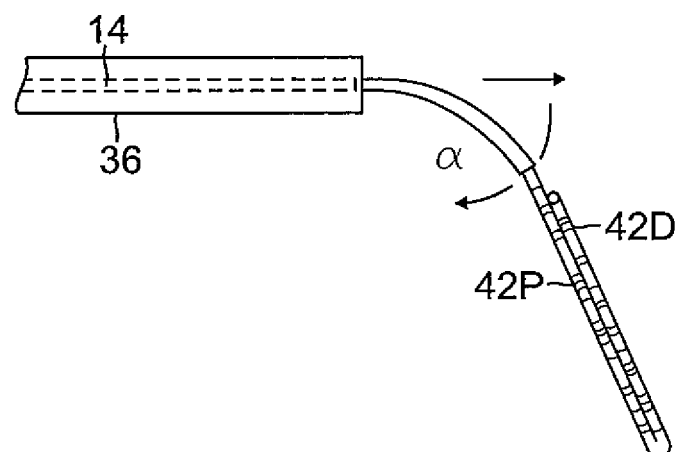
FIG. 4G is a top view of the distal section of FIG. 4E in a deflected configuration.

The tubular member 42 may be described as comprising a distal portion 42D and a proximal portion 42P. The flexible construction of the member 42 allows it to be generally straightened and advanced distally through a tube, for example, a guiding sheath 36 (FIG. 4A). As the distal portion 42D passes and exits the distal end of the guiding sheath 36, the distal portion 42D assumes a distal or first "S" configuration under its shape-memory (FIG. 4B). As the member 42 of the distal section 15 continues to be deployed, shape-memory of the member 42 causes the distal portion 42D to fold or flip back on the proximal portion 42P (FIG. 4C) via an angle θ equal to about 180 degrees. As the proximal portion 42P passes and exits the distal end of the guiding sheath 36, the proximal portion 42P assumes a proximal or second "S" configuration under its shape memory (FIGS. and). When both the distal and the proximal portions 42D and 42P are fully deployed, the first and second "S" configurations are stacked one above the other (FIG. 4F), with one "S" being upside down relative to the other, whereupon the member 42 assumes the predetermined 2D configuration resembling an infinity symbol effectively forming loop A and loop B in a side-by-side configuration (FIG. 4E). Loops A and B (and the distal and proximal portions 42D and 42B) lie generally in a common plane, which is also occupied by the intermediate deflection section 14 when in a neutral state (FIG. 4F), or the 2D configuration of the member 42 of the distal section 15 may be deflected at an angle α by the intermediate deflection section 14 so that they lie in different planes (FIG. 4G).

In another embodiment, as shown in FIGS. 11A-11D, the distal portion 42D forming the distal "S" configuration does not flip or fold back onto the proximal portion 42P forming the proximal "S" configuration. Rather, the curvature of the distal "S" configuration 42D is continuous with the curvature of the proximal "S" configuration 42P such that the two remain generally in the same plane as the distal section 15 is deployed.

Figure 5:
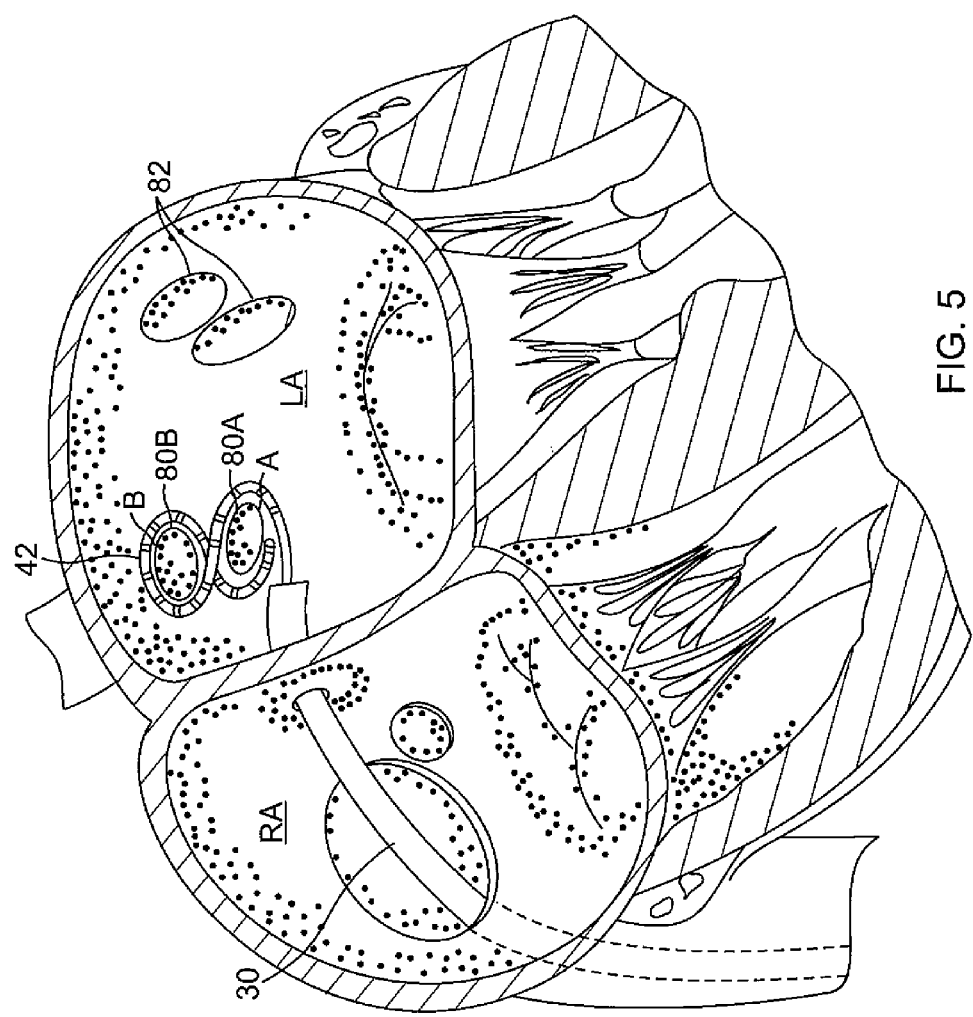
FIG. 5 is an illustration of a catheter of the present invention in use in the left atrium of the heart.

Regardless of the manner by which loops A and B are achieved, the 2D configuration of the distal section 15 is effectively positioned over a pair of adjacent ostia 80A and 80B of the pulmonary veins in the left atrium LA via a transceptal approach from the right atrium RA, as shown in FIG. 5. With loop A positioned over ostium 80A and loop B over ostium 80B, electrical signals in the regions of ostia A and B can be read simultaneously with the use of catheter 10 without the need for a second catheter. Where the catheter 10 is adapted for ablation, regions of ostia A and B may be ablated simultaneously with the catheter 10. The catheter 10 may be relocated to map and/or ablate pulmonary vein ostia 82A and 82B.

Figure 6A:
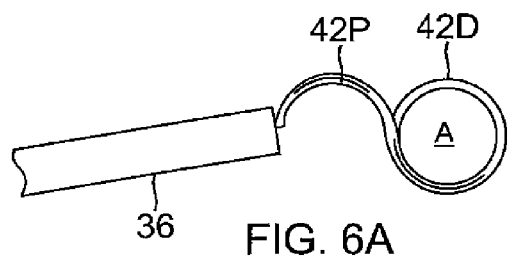
FIG. 6A is top plan view of a distal section, in accordance with another embodiment of the present invention, partially deployed from a guiding sheath.
Figure 6B:
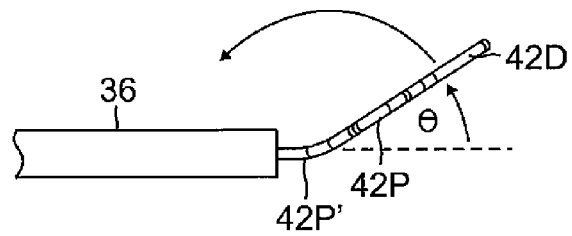
FIG. 6B is a side view of the distal section of FIG. 6A.
Figure 6C:
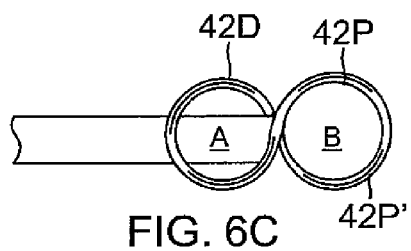
FIG. 6C is a side view of the distal section further deployed from the guiding sheath.
Figure 6D:
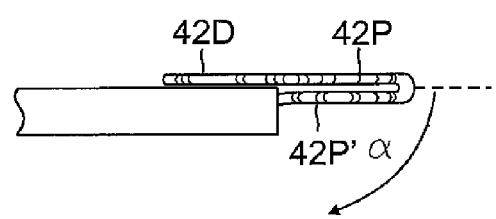
FIG. 6D is a side view of the distal section approaching full deployment from the guiding sheath.
Figure 6E:
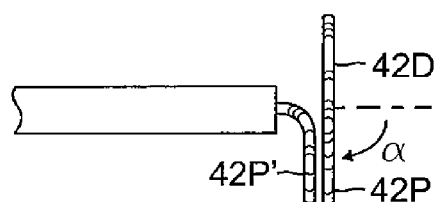
FIG. 6E is a side view of the distal section fully deployed from the guiding sheath.
Figure 6F:
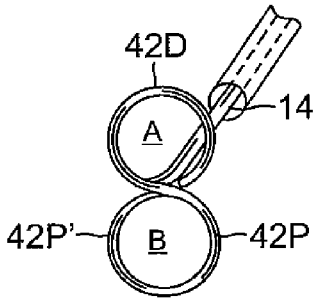
FIG. 6F is a front prospective view of the distal section of FIG. GE.
Figure 6G:
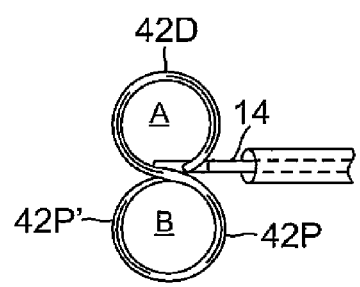
FIG. 6G is a side view of a distal section, in accordance with another embodiment of the present invention.

The 2D configuration resembling the infinity symbol may be achieved with a variety of different constructions, including those described below. In FIGS. 6A-6G, the member 42 of the distal section 15 has a different shape memory configuration to achieve the 2D configuration resembling the infinity symbol. In this embodiment, the member 42 has a distal portion 42D providing a generally closed loop or "O" configuration (FIG. 6A) and a first proximal portion 42P providing a first proximal "C" configuration extending generally in a common plane with the distal "O" configuration (FIG. 6A). As the portion 42P is fully deployed outside of the guiding sheath 36, the portions 42D and 42P fold over (under the shape memory of the member 42) via angle θ of about 180 degrees onto a more proximal portion 42P' (FIG. 6B) which provides a second "C" configuration opposite in orientation to the less proximal "C" configuration of the portion 42P, so as to achieve the 2D configuration resembling the infinity symbol. As the portion 42P' is fully deployed outside of the guiding sheath 36, the 2D configuration folds or flips under (under the shape memory of the distal section 15) via angle α of about 90 degrees to be generally perpendicular to the intermediate deflection section 14 (FIG. 6F). It is understood that the angle at which the 2D configuration extends from the intermediate deflection section 14 may be at any angle as desired or appropriate. For example, 2D configuration and the deflection section 14 can lie generally in the same common plane (FIG. 6G). That is, while the 2D configuration is transverse to the deflection section 14 thereby adopting a "T" configuration, the 2D configuration can lie in a different plane from the deflection section 14 (FIG. 6F) or lie in the same plane as the deflection section (FIG. 6G).

Figure 12A:
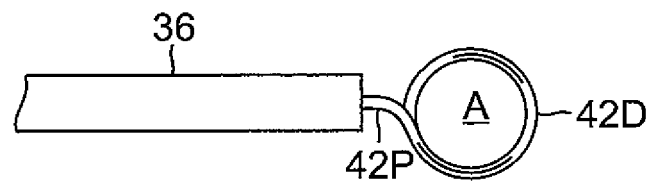
FIG. 12A is a side view of a distal section, in accordance with yet another embodiment of the present invention, partially deployed from a guiding sheath.
Figure 12B:
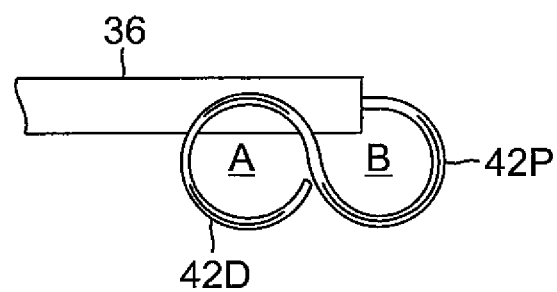
FIG. 12B is a side view of the distal section of FIG. 12A approaching full deployment from the guiding sheath.
Figure 12C:
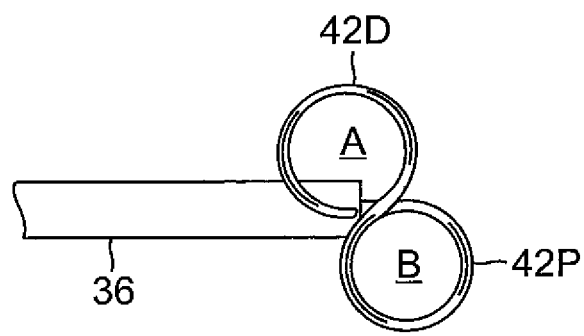
FIG. 12C is a side view of the distal section fully deployed from the guiding sheath.

In another embodiment, as shown in FIGS. 12A-12C, the distal portion 42D forming loop A does not flip or fold back. Rather, the curvature of the proximal portion 42P configuration 42D continues to form loop B. Comparing and contrasting the embodiments of FIGS. 11A-11D and FIGS. 12A-12D, the loops A and B of both embodiments remain in generally the same plane during deployment of the distal section 15, whereas a proximal end of 2D configuration can be at a location along an outer segment or arc of a loop (FIG. 11D) or at a location along an inner segment or arc of a loop (FIG. 12C).

FIG. 7A illustrate another embodiment wherein the distal section 15 has a distal portion 15D providing a first loop or "O" configuration in one direction (e.g., clockwise) (FIG. 6A) and a proximal portion 15P providing a second loop or "O" configuration in the opposite direction (e.g., counter-clockwise), both of which lie generally in a common plane as the intermediate deflection section 14, where the common location X of Loops A and B is generally aligned longitudinally with the deflection section 14.

FIG. 7B illustrates another embodiment wherein the distal section 15 has a distal portion 15D providing a first, loop A or "O" configuration in one direction (e.g., counterclockwise) (FIG. 6A) and a proximal portion 15P providing a second loop B or "O" configuration in the same direction (e.g., counterclockwise), both of which lie generally in a common plane that is generally perpendicular to the intermediate deflection section 14. Moreover, the common location X of Loops A and B is offset longitudinally from the deflection section 14.

Figure 8A:
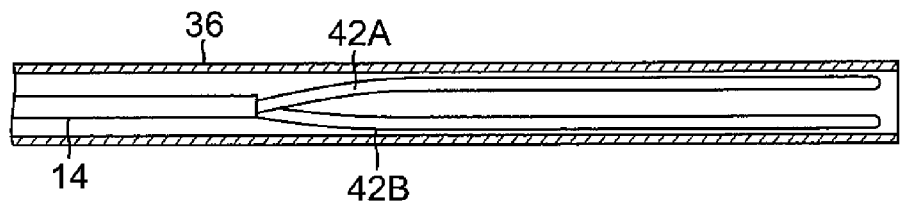
FIG. 8A is a top view of a distal section, in accordance with another embodiment of the present invention.
Figure 8B:
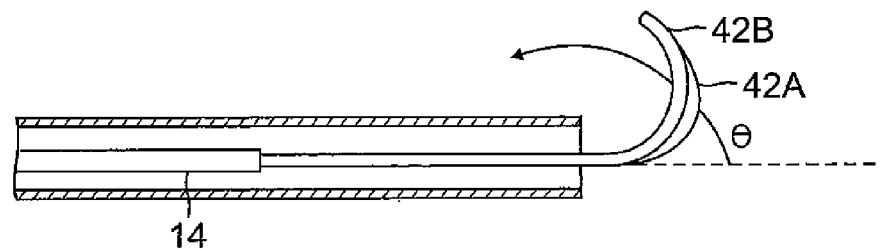
FIG. 8B is a side view of the distal section of FIG. 8A, partially deployed from the guiding sheath.
Figure 8C:
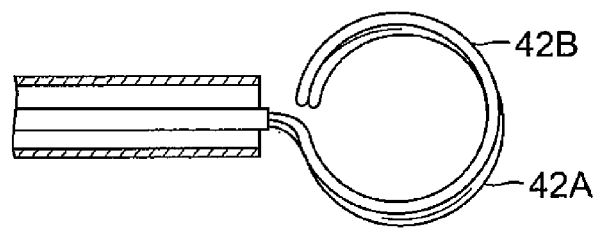
FIG. 8C is a side view of the distal section approaching full deployment from the guiding sheath.
Figure 8D:
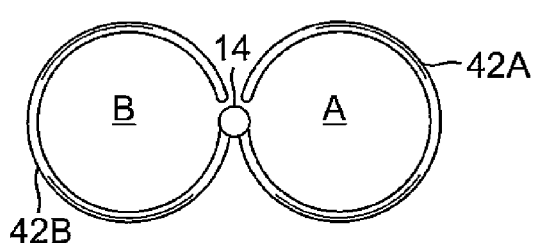
FIG. 8D is a front view of the distal section fully deployed from the guiding sheath.
Figure 8E:
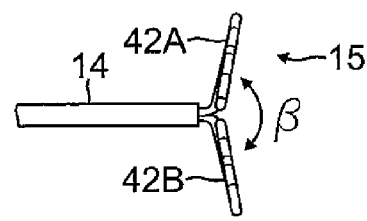
FIG. 8E is a top view of the distal section of FIG. 8D.
Figure 9A:
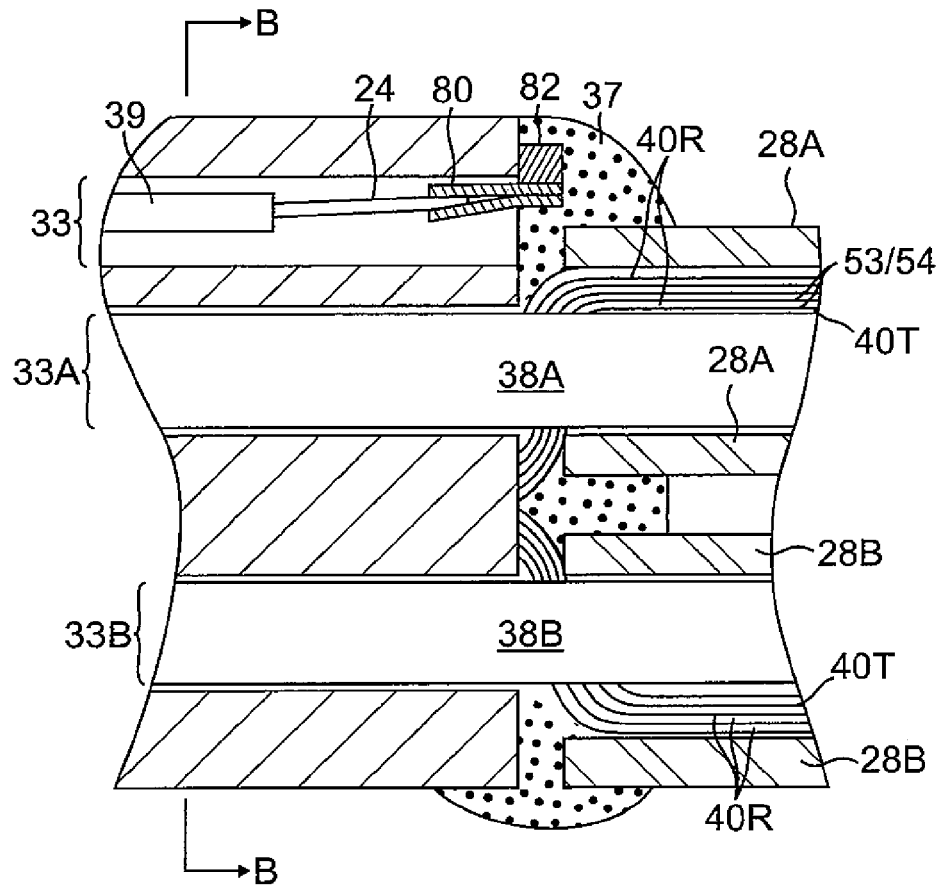
FIG. 9A is a side cross-sectional view of the distal section of FIG. 8A, including a junction with a deflection section.
Figure 9B:
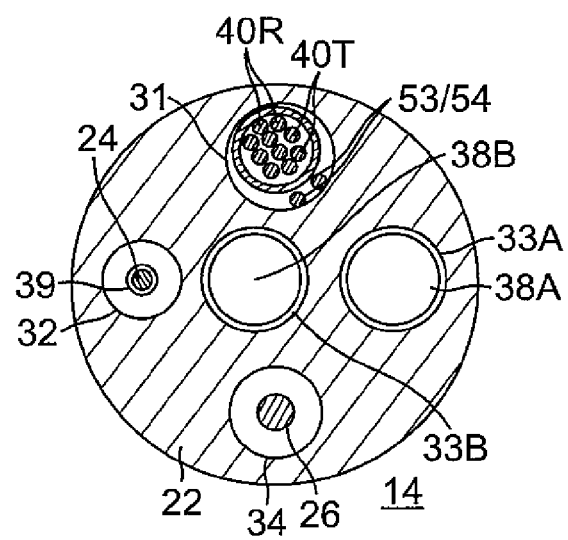
FIG. 9B is an end cross-sectional view of the deflection section of FIG. 9A.
Figure 10:
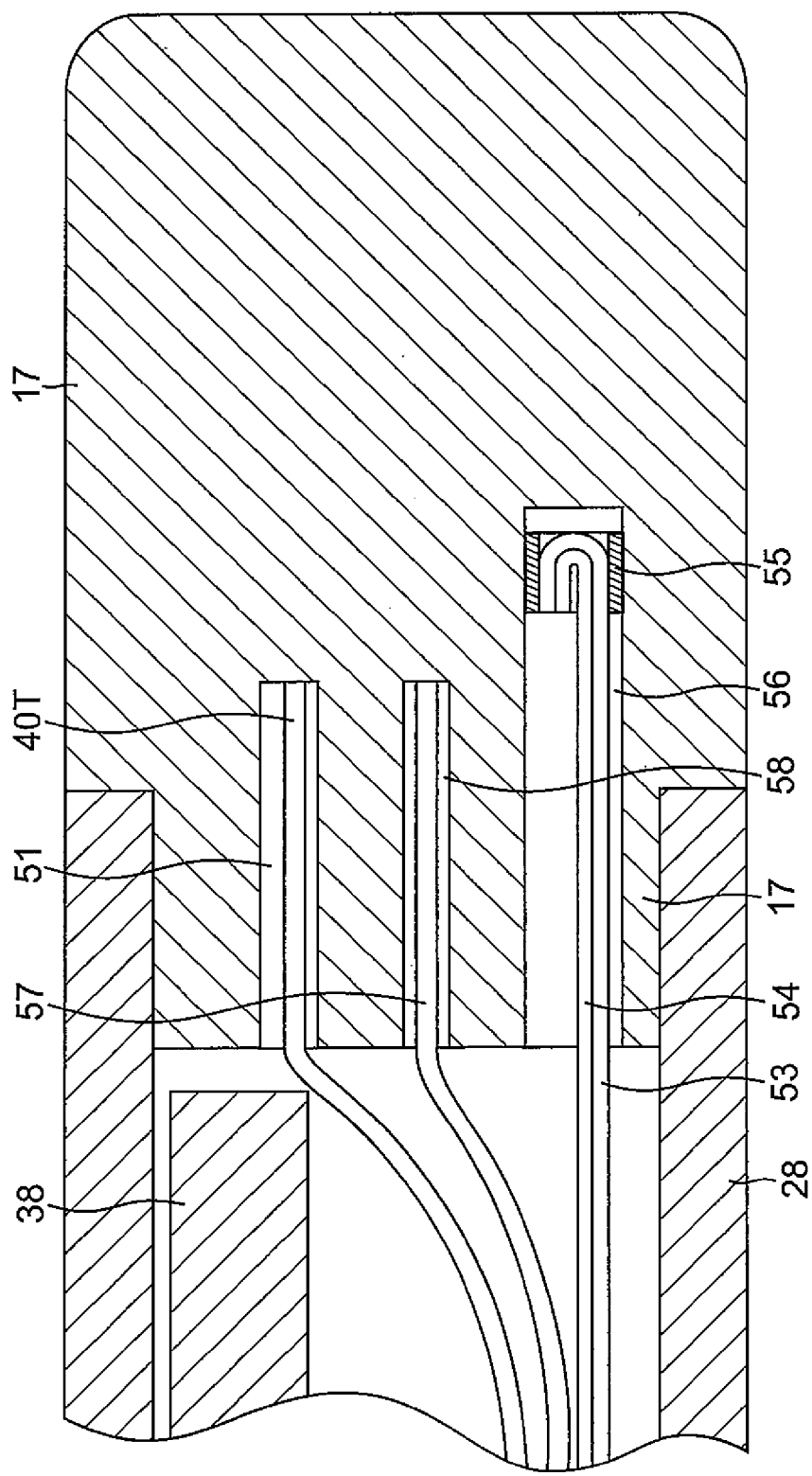
FIG. 10 is a side cross-sectional view of a tip electrode, in accordance with one embodiment of the present invention.
Figure 11A:
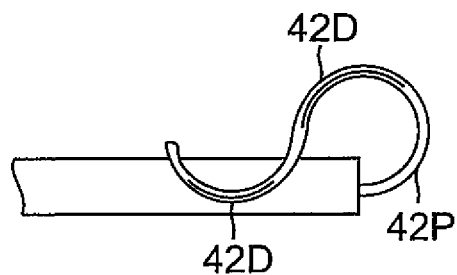
FIG. 11A is a side view of a distal section in accordance with another embodiment of the present invention, partially deployed from a guiding sheath.
Figure 11B:
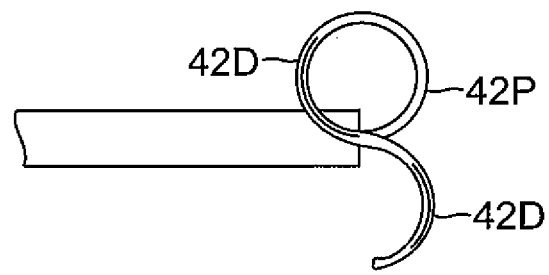
FIG. 11B is a side view of the distal section of FIG. 11A, further deployed from the guiding sheath.
Figure 11C:
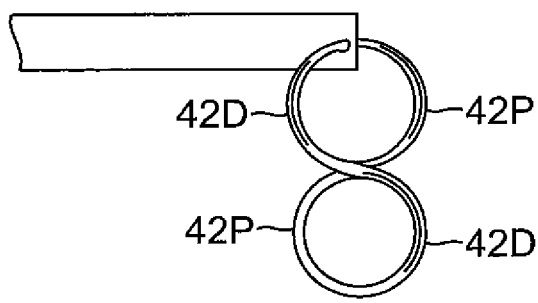
FIG. 11C is a side view of the distal section approaching full deployment from the guiding sheath.
Figure 11D:
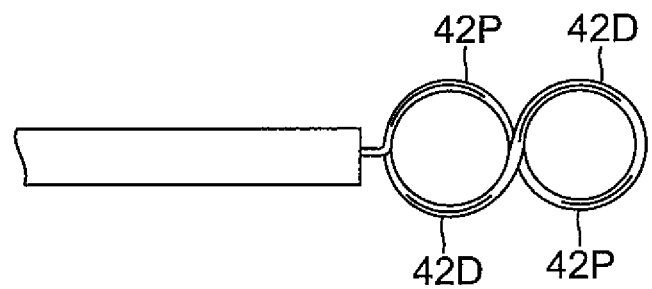
FIG. 11D is a side view of the distal section fully deployed from the guiding sheath.

FIGS. 8A-8E illustrate yet another embodiment wherein the distal section 15 comprises at least two generally parallel elongated flexible tubular members 42A and 42B extending from the distal end of the intermediate deflection section 14. As shown in FIGS. 10A and 10B, each member 42A and 42B has a respective elongated shape memory support member 38A and 38B and a respective nonconductive covering or tubing 28A and 28B. The flexible construction of the members 42A and 42B allows them each to be generally straightened and advanced distally through a tube, for example, a guiding sheath 36 (FIG. 8A). As the members 42A and 42B are fully deployed upon exiting the distal end of the guiding sheath 36 (FIG. 8B), their shape-memory begins to curve each of the members 42A and 42B back on itself into a loop or "O" configuration, and to separate from each other by pivoting outwardly from their proximal ends in opposite directions (FIGS. D and E). Separated by the angle 13 of about 180 degrees, loops A and B forming the 2D configuration generally resembling an infinity symbol lie generally in a common plane, with the deflection section 14 being generally perpendicular to the 2D configuration of distal section 15 (FIG. 8F). Again, it is understood that depending on the configuration of the junction between the intermediate deflection section 14 and the distal section 15, the 2D configuration of the distal section 15 and the deflection section 14 may be in a common plane, be perpendicular to each other, or, in fact, be at any angular orientation to each other, as needed or desired.

It is understood that the loops of 2D configuration of the distal section 15 need not be of the same size or same shape to each other. One loop may be smaller than the other(s). One loop may be more circular and the other(s) more oval. Each loop does not need to form a completely closed loop, but should be at least about 270 degrees, more preferably at least about 320 degrees, and more preferably at least about 340 degrees. Each loop carries one or more electrodes, for example, at least one ring electrode, for obtaining electrical data from the PV regions and/or ablating the same, and if desired or appropriate, a tip electrode.

The tip electrode 17 for any member 42 of the 2D configuration of the distal section 15 is mounted on a distal end of the member 42. As shown in FIG. 7, the tip electrode 17 has an exposed distal portion 17D, and a proximal stem 17P that extends into the non-conductive covering 28 and is fixed therein by polyurethane glue or the like.

The electrode lead wire 40T is connected at its distal end to the tip electrode 17. The distal end of the lead wire 40T is soldered in a first blind hole 51 in the proximal end of the tip electrode 17. The lead wire 40T extends between the non-conductive covering 28 and the support member 38. The proximal end of the lead wire 40T is electrically connected to a suitable connector (not shown) in the distal end of the control handle 16, which is connected to the source of ablation energy, e.g., RF energy, as is known in the art. The lead wire 40T extends through the lumen of the nonconductive covering 28, the first lumen 31 of the intermediate section 14, the central lumen 18 of the catheter body 12, and the control handle 16. In the depicted embodiment, the portion of the lead wire 40T extending through the central lumen 18 of the catheter body 12 and the lumen 31 of the intermediate section 14 may be enclosed within a protective sheath 84 to prevent contact with other components in the catheter. The protective sheath can be made of any suitable material, preferably polyimide. The protective sheath may be anchored at its distal end to the proximal end of the intermediate section 14 by gluing it in the first lumen 31 with polyurethane glue or the like. As would be recognized by one skilled in the art, the protective sheath can be eliminated if desired.

One or more ring electrodes 19 are mounted on the non-conductive covering 28 of the distal section 15 for mapping the region to be ablated before ablation, conducting ablation, and/or after ablation to assure that the resulting lesions blocked the electrical activity as desired. A description of a catheter including such ring electrodes is described in U.S. Pat. No. 8,545,495, entitled A Catheter Having Circular Ablation Assembly, the entire disclosure of which is incorporated herein by reference.

The ring electrodes 19 can be made of any suitable solid conductive material, such as platinum or gold, preferably a combination of platinum and iridium, and mounted onto the non-conductive cover 28 with glue or the like. Alternatively, the ring electrodes 19 can be formed by coating the non-conductive cover 28 with an electrically conducting material, like platinum, gold and/or iridium. The coating can be applied using sputtering, ion beam deposition or an equivalent technique.

In the embodiment of FIG. 3B, each ring electrode 19 is mounted by first forming a hole 62 in the non-conductive cover 28. A respective electrode lead wire 40R is fed through the hole 62, and the ring electrode 19 is welded in place over the lead wire 40R and the non-conductive cover 28. The lead wires 40R extend through the lumen of the non-conductive cover 28, the first lumen 31 of the intermediate deflection section 14, and through the central lumen 18 of the catheter body 12. The proximal end of each lead wire 40R is electrically connected to the suitable connector (not shown) in the control handle 16.

The number of ring electrodes 19 on the distal section 15 can vary as desired. Preferably the number of ring electrodes ranges from about six to about twenty, more preferably from about eight to about twelve. In one embodiment, the distal section 15 carries ten ring electrodes. The ring electrodes 19 can be approximately evenly spaced along the distal section 15. In one embodiment, a distance of approximately 5 mm is provided between the centers of adjacent ring electrodes 19.

In another embodiment, the distal section 15 includes a series of ring electrode pairs. Each ring electrode pair comprises two closely-spaced ring electrodes. As used herein, the term "ring electrode pair" refers to a pair of ring electrodes that are arranged closer to each other than they are to the other adjacent ring electrodes. Preferably the distance between two electrodes of an electrode pair is less than about 3 mm, more preferably less than about 2 mm, still more preferably from about 0.5 mm to about 1.5 mm. The number of electrode pairs can vary as desired, and preferably ranges from 6 to 14 pairs, more preferably 10 pairs.

The distal section 15 may carry 10 pairs of electrodes with a space of approximately 1 mm between the two electrodes of each pair. Preferably each ring electrode is relatively short, having a length ranging from about 0.4 mm to about 0.75 mm, with the most distal ring electrode being longer than the other ring electrodes, preferably having a length ranging from about 1 mm to about 1.5 mm. The longer ring electrode provides a visual reference to the user when the catheter is being viewed under fluoroscopy. By having one ring electrode, such as the most distal ring electrode, sized differently from the other ring electrodes, the user has a reference point when viewing the catheter under fluoroscopy.

Regardless of the size and number of the ring electrodes, the electrode pairs are preferably approximately evenly spaced along the distal section 15. The closely-spaced electrode pairs allow for more accurate detection of near field pulmonary vein potential versus far field atrial signals, which is very important when trying to treat atrial fibrillation. Specifically, the near field pulmonary vein potentials are very small signals whereas the atria, located very close to the pulmonary vein, provides much larger signals. Accordingly, even when the mapping array is placed in the region of a pulmonary vein, it can be difficult for the physician to determine whether the signal is a small, close potential (from the pulmonary vein) or a larger, farther potential (from the atria). Closely-spaced bipoles permit the physician to more accurately determine whether he is looking at a close signal or a far signal. Accordingly, by having closely-spaced electrodes, one is able to target exactly the locations of myocardial tissue that have pulmonary vein potentials and therefore allows the clinician to deliver therapy to the specific tissue. Moreover, the closely-spaced electrodes allow the physician to determine the exact anatomical location of the ostium/ostia by the electrical signal.

The pair of thermocouple wires 53 and 54 are provided for monitoring the temperature of any tip electrode 17. Any conventional temperature sensor, e.g., a thermocouple or thermistor, may be used. In the embodiment shown in FIG. 7, the thermocouple is formed by an enameled wire pair. One wire of the wire pair is a copper wire 53, e.g., a number "40 AWG" copper wire. The other wire of the wire pair is a constantan wire 54. The wires 53 and 54 of the wire pair are electrically isolated from each other except at their distal ends where they are twisted together, covered with a short piece of plastic tubing 55, e.g., polyimide, and covered with epoxy. The plastic tubing 55 is then attached in a second blind hole 56 of the tip electrode 17, by polyurethane glue or the like. Alternatively, the wires 53 and 54 can be soldered into the second blind hole 56 or otherwise attached to the tip electrode 17. The wires 53 and 54 extend through the first lumen 31 in the intermediate section 14 (FIG. 3C) and through the central lumen 18 of the catheter body 12 along with the lead wire 40T and 40R (FIG. 2A). The wires 53 and 54 then extend out through the control handle 16 and to a connector (not shown) connectable to a temperature monitor (not shown).

Additionally, a safety wire 57 is provided to further secure the tip electrode 17 to the distal section 15 and assure that the tip electrode does not detach from the catheter. The safety wire is preferably a metal wire having its distal end soldered in a third blind hole 58 in the tip electrode 17 and its proximal end soldered or otherwise attached in the control handle 16. In the depicted embodiment, the safety wire 57 extends through the first lumen 31 in the intermediate section 14 (FIG. 3C) and through the central lumen 18 of the catheter body 12 (FIG. 2A) along with the lead wires 40T and 40R and thermocouple wires 53 and 54. Other arrangements for attaching the safety wire can be provided, as would be recognized by one skilled in the art, or the safety wire can be eliminated.

An electromagnetic position sensor 30 is housed in the lumen of the nonconductive covering 28 at or near its distal end, just proximal of the tip electrode 17. The sensor cable 26 extends from the sensor 30 and through the lumen of the covering 28 (FIG. 3B), the lumen 34 of the tubing 22 of the deflection section 14 (FIG. 2C), the lumen 18 of the catheter body 12 (FIG. 2A) and into the control handle 16

The puller wire 24 is provided for deflection of the intermediate section 14. The puller wire 24 extends through the catheter body 12, is anchored at its proximal end to the control handle 16, and is anchored at its distal end to a distal end of the intermediate section 14. The puller wire 24 is made of any suitable metal, such as stainless steel or Nitinol, and is preferably coated with TEFLON or the like. The coating imparts lubricity to the puller wire 24. The puller wire 24 preferably has a diameter ranging from about 0.006 to about 0.010 inch.

A compression coil 66 is situated within the catheter body 12 in surrounding relation to the puller wire 24, as shown in FIG. 2B. The compression coil 66 extends from the proximal end of the catheter body 12 to the proximal end of the intermediate section 14. The compression coil 66 is made of any suitable metal, preferably stainless steel. The compression coil 66 is tightly wound on itself to provide flexibility, i.e., bending, but to resist compression. The inner diameter of the compression coil 66 is preferably slightly larger than the diameter of the puller wire 24. The Teflon coating on the puller wire 24 allows it to slide freely within the compression coil 66. The outer surface of the compression coil 66 is covered by a flexible, non-conductive sheath 68, e.g., made of polyimide tubing.

The compression coil 66 is anchored at its proximal end to the outer wall 20 of the catheter body 12 by a proximal glue joint (not shown) and at its distal end to the intermediate section 14 by a distal glue joint 72. Both glue joints may comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 20 of the catheter body 12 which is heated sufficiently to form a permanent hole. The glue is then introduced through the hole to the outer surface of the compression coil 66 and wicks around the outer circumference to form a glue joint about the entire circumference of the compression coil.

The puller wire 24 extends into the second lumen 32 of the intermediate section 14. In the illustrated embodiment, the puller wire 24 is anchored at its distal end to the distal end of the intermediate section 14, as shown in FIG. 3. Specifically, a T-shaped anchor is formed, which comprises a short piece of tubular stainless steel 80, e.g., hypodermic stock, which is fitted over the distal end of the puller wire 64 and crimped to fixedly secure it to the puller wire. The distal end of the tubular stainless steel 80 is fixedly attached, e.g., by welding, to a cross-piece 82 formed of stainless steel ribbon or the like. The cross-piece 82 sits beyond the distal end of the second lumen 32. The cross-piece 82 is larger than the lumen opening and, therefore, cannot be pulled through the opening. The distal end of the second lumen 32 is then filled with glue or the like, preferably a polyurethane glue 37. Within the second lumen 32 of the intermediate section 14, the puller wire 24 extends through a plastic, preferably Teflon, puller wire sheath 39, which prevents the puller wire 24 from cutting into the wall of the tubing 22 of the deflection section 14 when the deflection section is deflected.

Longitudinal movement of the puller wire 24 relative to the catheter body 12, which results in deflection of the intermediate section 14, is accomplished by suitable manipulation of the control handle 16. Examples of suitable control handles for use in the present invention are disclosed, for example, in U.S. Pat. Nos. Re 34,502 and 5,897,529, the entire disclosures of which are incorporated herein by reference. It is understood that where bi-directional deflection is desired, the catheter may be configured to provide a second puller wire that passes through a lumen (generally diametrically opposite of the lumen 32 for the first puller wire 24) in the deflection section 14 and is responsive to the control handle 16.

In use, a suitable guiding sheath 36 is inserted into the patient with its distal end positioned at a desired mapping and/or ablation location, as shown in FIG. 5. An example of a suitable guiding sheath for use in connection with the present invention is the Preface Braided Guiding Sheath, commercially available from Biosense Webster, Inc. (Diamond Bar, Calif.). The distal end of the sheath is guided into the right atrium RA and then into the left atrium LA via a transceptal approach. The catheter 10 is passed through the guiding sheath 36. In particular, as the distal section 15 of the catheter is fed into the proximal end of the guiding sheath 36, the member(s) 42 of the distal section 15 are straightened to fit through the sheath 36. After the distal section 15 of the catheter is positioned at the desired location in the left atrium LA, the guiding sheath 36 is pulled proximally, exposing at least the distal section 15, if not also the deflectable intermediate section 14, as needed. Outside of the guiding sheath 36, the distal section 15 assumes the 2D configuration under its shape memory providing at least loops A and B. The user then manipulates the catheter to position the 2D configuration of the distal section 15 such that each loop sits over a respective ostium. With the distal section 15 in contact with the ostia, electrical activity in the regions of at least two ostia can be sensed simultaneously by the electrodes on the loops A and B without the use of a second catheter. If desired, the electrodes also can be energized to ablate in the regions of at least two ostia simultaneously without the use of a second catheter.

If desired, two or more puller wires can be provided to enhance the ability to manipulate the intermediate section. In such an embodiment, a second puller wire and a surrounding second compression coil extend through the catheter body and into an additional off-axis lumen in the intermediate section. Suitable designs of catheters having two or more puller wires, including suitable control handles for such embodiments, are described, for example, in U.S. Pat. Nos. 6,123,699; 6,171,277; 6,183,435; 6,183,463; 6,198,974; 6,210,407 and 6,267,746, the entire disclosures of which are incorporated herein by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Also, different features of different embodiments may be combined as needed or appropriate. Moreover, the catheters described herein may be configured to apply various energy forms, including microwave, laser, RF and/or cryogens. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
   an elongated catheter body;
   a distal section distal of the elongated catheter body, the distal section having a flexible elongated member with shape memory, the member being configured to assume a 2D configuration resembling an infinity symbol and terminating in a free distal end; and
   at least one electrode mounted on the member.

2. The catheter of claim 1, wherein the 2D configuration resembles a first loop and a second loop, wherein the first and second loops are side-by-side, generally extending in a common plane.

3. The catheter of claim 1, wherein the member has a distal S configuration and a proximal S configuration, wherein the S configurations are stacked on each other, and one of the S configurations is reversed.

4. The catheter of claim 1, wherein the member has a distal O configuration, a first proximal C configuration and a second proximal C configuration, wherein the first and second C configurations face each other.

5. The catheter of claim 1, further comprising a deflection section proximal of the distal section.

6. The catheter of claim 5, wherein the 2D configuration and the deflection section are generally in a common plane.

7. The catheter of claim 5, wherein the 2D configuration and the deflection section are generally perpendicular to each other.

8. The catheter of claim 5, wherein the 2D configuration has a first loop, a second loop and an intersection between the first and second loops.

9. The catheter of claim 8, wherein the intersection is generally aligned with a longitudinal axis of the deflection section.

10. The catheter of claim 8, wherein the intersection is offset from a longitudinal axis of the deflection section.

11. A catheter comprising:
    an elongated catheter body;
    a distal section distal of the elongated catheter body and having at least first and second flexible elongated members with shape memory, the at least first and second flexible elongated members being configured to assume a 2D configuration resembling an infinity symbol, wherein the first elongated member is configured to form a first loop terminating in a first free distal end of the first elongated member and the second elongated member is configured to form a second loop terminating in a second free distal end of the second elongated member, the first and second loops being side-by-side having an intersection, the first and second free distal ends being generally at the intersection, and the 2D configuration being generally perpendicular to the catheter body; and at least one electrode mounted on at least one of the at least first and second elongated members.

12. The catheter of claim 11, wherein the first and second loops lie generally in a common plane.

13. A catheter comprising:

an elongated catheter body;

a distal section distal of the elongated catheter body and having a flexible elongated member with shape memory, the member being configured to assume a 2D configuration terminating in a free distal end, the 2D configuration having a first loop and a second loop in which the first and second loops generally lie in a common plane; and at least one electrode on each of the first and second loops.

14. The catheter of claim 13, wherein the member has a distal S configuration and a proximal S configuration, wherein one of the S configurations is configured to lie against the other S configuration to form the 2D configuration with the first and second loops.

15. The catheter of claim 13, wherein the member has a distal C configuration, a less proximal O configuration and a more proximal C configuration, wherein the distal and proximal C configurations form a first loop and the proximal O configuration forms the second loop.

16. The catheter of claim 13, wherein the member has a distal O configuration that forms the first loop and a proximal O configuration forms the second loop.

* * * * *